United States Patent [19]

Helsley et al.

[11] Patent Number: 4,916,139

[45] Date of Patent: Apr. 10, 1990

[54] 3-(2,3,4,5,6-PENTAFLUOROPHENOXY)-8-AZABICYCLO(3.2.1)OCTANES

[75] Inventors: Grover C. Helsley, Pluckemin; Larry Davis, Sergeantsville; Gordon E. Olsen, Somerset, all of N.J.

[73] Assignee: Hoechst-Roussel Pharmaceuticals, Inc., Somerville, N.J.

[21] Appl. No.: 362,639

[22] Filed: Jun. 7, 1989

Related U.S. Application Data

[62] Division of Ser. No. 167,942, Mar. 14, 1988, Pat. No. 4,861,889.

[51] Int. Cl.$^4$ ................ A61K 31/495; A61K 31/435; C07D 401/06
[52] U.S. Cl. .................................... 514/299; 514/253; 544/362; 546/183
[58] Field of Search ................. 514/253, 299

*Primary Examiner*—Cecilia Shen
*Attorney, Agent, or Firm*—Elliott Korsen

[57] ABSTRACT

3-(2,3,4,5,6-pentafluorophenoxy)-8-azabicyclo[3.2.1]octanes and methods for treating depression, convulsions, pain, and hypertension utilizing compounds or compositions thereof are disclosed.

8 Claims, No Drawings

3-(2,3,4,5,6-PENTAFLUOROPHENOXY)-8-AZABICYCLO(3.2.1)OCTANES

This is a division, of application Ser. No. 167,942 filed March 14, 1988, now U.S. Pat. No. 4,861,889.

This invention relates to 3-(2,3,4,5,6-pentafluorophenoxy)-8-azabicyclo[3.2.1]octanes of the formula:

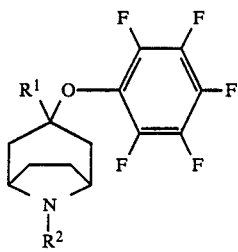

FORMULA I wherein $R^1$ is hydrogen or aryl and $R^2$ is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminothiocarbonyl, (loweralkylamino)thiocarbonyl, (diloweralkylamino)thiocarbonyl; (arylamino)thiocarbonyl, aminoloweralkyl, (loweralkylamino)loweralkyl, (diloweralkylamino)loweralkyl, (diloweralkylphosphinyl)loweralkyl, a group of the formula

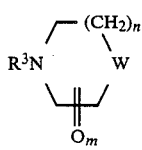

wherein n is an integer having a value of zero or 1, m is an integer having a value of zero or 1, W is $CH_2$ or $NR^{3a}$ wherein $R^{3a}$ is hydrogen, loweralkyl or aryl, and $R^3$ is loweralkylene, loweralkenylene or loweralkynylene, and a group of the formula

wherein $R^4$ is $CH(Cl)CH_3$; which compounds are useful as analgesic, antidepressant, anticonvulsant, and antihypertensive agents. In further embodiments this invention relates to pharmaceutical compositions containing said 3-(2,3,4,5,6-pentafluorophenoxy-8-azabicyclo[3.2.1]octanes as an active ingredient, as well as to methods of treating depression, convulsions, pain and hypertension with pharmaceutically effective amounts of such a compound.

Absent the designation of a specific isomeric form, a given chemical formula or name is herein defined as encompassing all stereo, optical, and geometrical isomers thereof. As used herein, a given chemical formula or name encompasses the pharmaceutically acceptable acid addition salts and solvates (e.g. hydrates) thereof.

Subgeneric to the 3-(2,3,4,5,6-pentafluorophenoxy-8-azabicyclo[3.2.1]octanes of this invention are Formula I compounds wherein:

(a) $R^1$ is hydrogen;
(b) $R^1$ is aryl;
(c) $R^2$ is hydrogen;
(d) $R^2$ is loweralkyl;
(e) $R^2$ is arylloweralkyl;
(f) $R^2$ is

wherein A is oxygen or sulfur and $R^5$ is hydrogen, loweralkyl, or arylloweralkyl;

(g) $R^2$ is

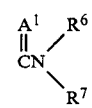

wherein $A^1$ is oxygen or sulfur and $R^6$ and $R^7$ are independently hydrogen or loweralkyl;

(h) $R^2$ is

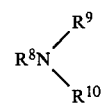

wherein $R^8$ is loweralkylene and $R^9$ and $R^{10}$ are independently hydrogen or loweralkyl;

(i) $R^2$ is

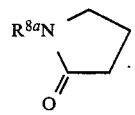

wherein $R^{8a}$ is loweralkylene, loweralkenylene or loweralkynylene;

(j) $R^2$ is

wherein $R^4$ is $CH(Cl)CH_3$;

(k) $R^2$ is

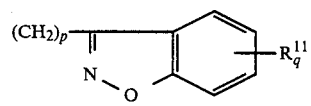

wherein p is an integer having a value of 2 or 3, q is an integer having a value of zero to 2 inclusive, and $R^{11}$ is halogen, loweralkyl or loweralkoxy;

(l) $R^2$ is

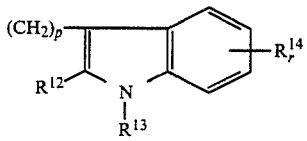

wherein p is an integer having a value of 2 or 3, r is an integer having a value of zero or 1, $R^{12}$ and $R^{13}$ are independently hydrogen or loweralkyl, and $R^{14}$ is halogen or loweralkyl (m) $R^2$ is

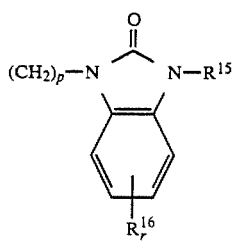

wherein p is an integer having a value of 2 or 3, r is an integer having a value of zero or 1, $R^{15}$ is hydrogen or loweralkyl, and $R^{16}$ is halogen or loweralkyl;

(n) $R^2$ is (diloweralkylphosphinyl)loweralkyl;
(o) $R^2$ is

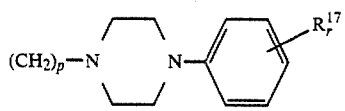

wherein p is an integer having a value of 2 or 3, r is an integer having a value of zero or 1, and $R^{17}$ is halogen, loweralkyl, or loweralkoxy and;

(p) $R^2$ is

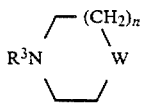

wherein n is an integer having a value of zero or 1, W is $CH_2$ or $NR^{3a}$ wherein $R^{3a}$ is hydrogen, loweralkyl, or aryl, and $R^3$ is loweralkylene, loweralkenylene or loweralkynylene.

As used throughout the specification and appended claims the term "loweralkyl" shall mean a linear or branched, acyclic hydrocarbon radical containing no unsaturation and having the formula $-C_xH_{2x+1}$ wherein x is an integer having a value of 1 to 7, inclusive, such as methyl, ethyl, 1-propyl, 2-propyl, 1-butyl, 1-pentyl, 2-pentyl, 3-hexyl, 4-heptyl, and the like; the term "loweralkoxy" shall mean an acyclic organic radical of the formula $-OC_xH_{2x+1}$ wherein x is an integer having a value of 1 to 7, inclusive, such as methoxy, ethoxy, 1- and 2-propoxy, 1,2-dimethylethoxy, 1-butoxy, 1- and 2-pentoxy, 3-hexoxy, 4-heptoxy and the like; the term "halogen" shall mean a member of the group consisting of fluorine, chlorine, bromine, and iodine radicals; the term "aryl" shall mean a phenyl group optionally substituted by one or more substituents selected from the group consisting of halogen, loweralkyl, loweralkoxy, and trifluoromethyl; the term "arylloweralkyl" shall mean a loweralkyl group having an aryl substituent thereon; the term "heteroaryl" shall mean an aromatic heterocyclic mono- or dicyclic radical such as, for example, benzisoxazolyl, indolyl, benzimidazolyl, and the like, optionally substituted by one or more substituents selected from the group consisting of halogen, loweralkyl, and loweralkoxy; the term "heteroarylloweralkyl" shall mean a loweralkyl group having a heteroaryl substituent thereon; the term "cycloalkyl" shall mean a saturated carbocyclic group having from 3 to 7 carbon atoms such as cyclopropyl, cyclobutyl, cyclopentyl, cyclohexyl and cycloheptyl; the term "cycloalkylloweralkyl" shall mean a loweralkyl group having a cycloalkyl substituent thereon; the term "amino" shall mean a group of the formula $-NH_2$; the term "aminocarbonyl" shall mean a group of the formula $-C(O)NH_2$; the term "aminothiocarbonyl" shall mean a group of the formula $-C(S)NH_2$; the term "loweralkylamino" shall mean an amino group substituted at the nitrogen atom thereof by a loweralkyl group; the term "diloweralkylamino" shall mean an amino group substituted at the nitrogen atom thereof by two loweralkyl groups; the term "arylloweralkylamino" shall mean an amino group substituted at the nitrogen atom thereof by an arylloweralkyl group; the term "loweralkylene" shall mean a saturated linear or branched hydrocarbon radical having 1 to 7 carbon atoms, inclusive; the term "loweralkenylene" shall mean a linear or branched chain bivalent hydrocarbon radical having 2 to 7 carbon atoms, inclusive and a carbon-carbon double bond; the term "loweralkynylene" shall mean a linear or branched chain bivalent hydrocarbon radical having 2 to 7 carbon atoms and a carbon-carbon triple bond; and the term "diloweralkylphosphinyl" shall mean a group of the formula

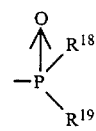

wherein $R^{18}$ and $R^{19}$ are loweralkyl.

The 3-(2,3,4,5,6-pentafluorophenoxy)-8-azabicyclo[3.2.1]octanes of this invention are synthesized by the process illustrated in the Reaction Schemes which follow.

As illustrated in Reaction Scheme A, the endo-isomers of the compounds of this invention are synthesized by reacting an anion of 3-hydroxy-8-methyl-8-azabicyclo[3.2.1]octane 1 with hexafluorobenzene 2 to yield an endo-3-(2,3,4,5,6-pentafluorophenoxy)-8-methyl-8-azabicyclo[3.2.1]octane 3 which is converted to the corresponding 8-(α-chloroethoxycarbonyl)-derivative 4 and then decarboxylated to an endo-3-(2,3,4,5,6-pentafluorophenoxy)-8-azabicyclo[3.2.1]octane 5 from which a variety of 8-substituted derivatives 6 may be produced.

To generate the anion of the starting alcohol 1, the alcohol is reacted with an alkali metal hydride (e.g. lithium hydride, potassium hydride, sodium hydride, and the like, sodium hydride being preferred) or a suitable organolithium compound (e.g. butyllithium or phenyllithium) at a temperature of from about 10° C. to about 80° C., preferably from about 60° C. to about 70° C., in an appropriate organic solvent. Suitable solvents include dipolar aprotic solvents such as hexamethylphosporamide, dimethylsulfoxide, dimethylformamide, and the like, dimethylformamide being preferred. The resulting anion is thereafter reacted with hexafluorobenzene 2 at a temperature of from about −80° C. to about 0° C., preferably from about −70° C. to about −60° C., in the solvent medium previously described.

The reaction of the 8-methyl derivative 3 with α-chloroethylchloroformate to produce the corresponding 8-chloroethoxycarbonyl derivative 4 is conducted at a temperature of from about 0° C. to about 100° C., preferably from about 50° C. to about 80° C. in the presence of an appropriate organic solvent. Suitable solvents include halogenated hydrocarbons such as, for example, dichloromethane, chloroform, carbontetrachloride, and the like, chloroform being preferred.

Decarboxylation of the 8-chloroethoxycarbonyl derivative 4 is ordinarily accomplished by heating same in a suitable solvent (e.g. alkanols such as methanol, ethanol, 1- and 2-propanol, an the like; methanol being preferred) at a temperature of from about 30° C. to the reflux temperature of the solvent medium. Reflux temperatures are preferred.

Substitution at the 8- position of the endo-3-(2,3,4,5,6-pentafluorophenoxy)-8-azabicyclo[3.2.1]octane 5 may be accomplished by any of numerous methods known in the art.

To provide Formula I compounds wherein $R^2$ is a formyl radical, the 3-(2,3,4,5,6-pentafluorophenoxy)-8-azabicyclo[3.2.1]octane 5 can be treated with a mixed acetic-formic acid anhydride at a temperature of from about 0° C. to about 30° C. Preferably, the mixed anhydride is utilized in situ following the reaction of formic acid and acetic anhydride at a temperature of from about 5° C. to about 25° C.

The reaction of 3-(2,3,4,5,6-pentafluorophenoxy)-8-azabicyclo[3.2.1]octane 5 and nitrourea in an alkanol (e.g. methanol, ethanol, 1-propanol, 2-propanol, and the like; methanol being preferred) at a temperature of from about 20° C. to about 100° C., preferably from about 50° C. to about 80° C., provides a means of a furnishing an 8-aminocarbonyl-3-(2,3,4,5,6-pentafluorophenoxy)-8-azabicyclo[3.2.1]octane 6.

To synthesize a Formula I compound wherein $R^2$ is a radical selected from the group consisting of loweralkyl, cycloalkylloweralkyl, arylloweralkyl, heteroarylloweralkyl, (diloweralkylphosphinyl)loweralkyl, (loweralkylamino)loweralkyl, (diloweralkylamino)loweralkyl, loweralkylcarbonyl, loweralkoxycarbonyl, (arylloweralkyl)carbonyl, (loweralkylamino)carbonyl, (diloweralkylamino)carbonyl, (arylamino)carbonyl, loweralkylthiocarbonyl, loweralkoxythiocarbonyl, (arylloweralkyl)thiocarbonyl, (loweralkylamino)thiocarbonyl (diloweralkylamino)thiocarbonyl and (arylamino)thiocarbonyl, a 3-(2,3,4,5,6-pentafluorophenoxy)-8-azabicyclo[3.2.1]octane 5 is reacted with a compound of the formula $XC(O)R^{20}$, $XC(S)R^{21}$, or $XR^{22}$ (wherein X is halogen, preferably chlorine; $R^{20}$ and $R^{21}$ are loweralkyl, arylloweralkyl, loweralkoxy, loweralkylamino, diloweralkylamino or arylamino; and $R^{22}$ is loweralkyl, cycloalkylloweralkyl, arylloweralkyl, heteroarylloweralkyl, (diloweralkylphosphinyl)-loweralkyl, (loweralkylamino)loweralkyl, or (diloweralkylamino)loweralkyl in a suitable organic solvent (e.g. halocarbons or polar aprotic solvents such as methylene chloride, dichloroethane, dichloromethane, chloroform, hexamethylphosphoramide, dimethylacetamide, dimethylformamide, dimethylsulfoxide, and the like). Typically, the reaction is conducted at a temperature of from about 0° C. to about 100° C., optimal reaction temperatures are, however, subject to variation depending upon the particular solvent employed. Temperatures of from about 20° C. to about 80° C. are generally preferred for reactions conducted in the presence of a polar aprotic solvent (e.g. dimethylformamide), whereas, reactions conducted in a halocarbon (e.g. dichloromethane) are frequently conducted at room temperatures. The reaction is generally in the presence of an acid acceptor (e.g. tertiary amines, and alkali metal carbonates and bicarbonates such as triethylamine, potassium carbonate, sodium carbonate, sodium bicarbonate, and the like. If desired, a promotor such as, for example, potassium iodide, may also be employed. The solubility of reactants, acid acceptors, and promotors in a given solvent will determine whether or not the use of a co-solvent is advisable. For example, water can be used as a co-solvent when employing an alkali metal carbonate promotor in a chloroform solvent.

Arylloweralkyl and heteroarylloweralkyl substitution is alternatively achieved by reacting a phenyl sulfonate of the formula $R^2OS(O)OC_6H_5$ (wherein $R^2$ is arylloweralkyl or heteroarylloweralkyl) with a 3-(2,3,4,5,6-pentafluorophenoxy)-8-azabicyclo[3.2.1]octane 5. The reaction is generally conducted in a polar aprotic solvent (e.g. dimethylformamide, hexamethylphosphoramide, dimethylacetamide, dimethylsulfoxide, and the like; dimethylsulfoxide being preferred) at a temperature of from about 0° C. to about 100° C., preferably from about 50° C. to about 85° C. The reaction is ordinarily conducted in the presence of an alkali metal carbonate or bicarbonate (e.g. potassium carbonate, sodium carbonate, sodium bicarbonate, and the like; potassium carbonate being preferred).

Formula I compounds wherein $R^2$ is a radical of the formula

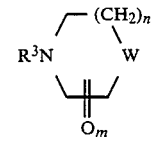

wherein n, W and $R^3$ are as previously defined are produced by a variety of reactions tailored to the partiuclar functional group $R^2$. Thus, a formula I compound wherein $R^2$ is

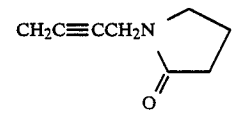

is produced by the reaction of 3-(2,3,4,5,6-pentafluorophenoxy)-8-azabicyclo[3.2.1]octane 5 with 1-(butynyl)-pyrrolin-2-one and paraformaldehyde. The reaction is generally conducted in a non-reactive organic solvent (e.g. etheral solvents such as diethyl ether, tetrahydrofuran, dioxane, and the like; p-dioxane being preferred) at a temperature of from about 20° C. to about 100° C., preferably from about 80° C. to about 100° C. If desired, the reaction is conducted in the presence of a suitable promoter (e.g. copper (I) chloride).

Formula I compounds wherein $R^2$ is loweralkylaminocarbonyl or loweralkylaminothiocarbonyl are produced by reacting a 3-(2,3,4,5,6-pentafluorophenoxy)-8-azabicyclo[3.2.1]octane 5 with an isocyanate or isothiocyanate of the formula RN=C=O or RN=C=S (R being loweralkyl). The reaction is generally conducted in the presence of an aromatic solvent (e.g. benzene, toluene, xylene, and the like, benzene being preferred) at a temperature of from about 10° C. to about 80° C.

To furnish 8-cyano-3-(2,3,4,5,6-pentafluorophenoxy)-8-azabicyclo[3.2.1]octanes, a 3-(2,3,4,5,6-pentafluorophenoxy)-8-azabicyclo[3.2.1]octane 5 is reacted with a cyanogen halide such as cyanogen bromide or cyanogen chloride. The reaction is generally conducted in a halocarbon solvent (e.g. dichloromethane, dichloroethane, chloroform, and the like) at a temperature of from about 0° C. to about 60° C. in the presence of an acid acceptor (e.g. metal carbonates or bicarbonates as previously described).

Reaction Scheme B illustrates the synthesis of the exo-isomers of this invention. As illustrated, a 3-hydroxy-8-methyl-8-azabicyclo[3.2.1]octane 1 is reacted with pentafluorophenol 7 to produce an exo-3-(2,3,4,5,6-pentafluorophenoxy)-8-methyl-8-azabicyclo[3.2.1]octane 8 which is converted to the corresponding 8-(α-chloroethoxycarbonyl) derivative 9, and decarboxylated to an exo-3-(2,3,4,5,6-pentafluorophenoxy)-8-azabicyclo[3.2.1]octane 10 from which a variety of exo-8-substituted derivatives 11 may be produced.

The reaction of 3-hydroxy-8-methyl-8-azabicyclo[3.2.1]octane 1 with pentafluorophenol 7 is conducted in the presence of triphenylphosphine and diethylazodicarboxylate. Desirably triphenylphosphine and diethylazodicarboxylate are utilized in quantities slightly in excess of stoichiometiric amounts; the use of about a 10% excess of triphenylphosphine and diethylazodicarboxylate being preferred. The reaction is generally conducted in a non-reactive organic solvent at a temperature of from about 0° C. to about 50° C., preferably from about 0° C. to about 5° C. Suitable solvents include aromatic hydrocarbons as previously described; benzene being preferred.

The resultant exo-8-methyl-3-(pentafluorophenoxy)-derivative 8 may be subjected to the carboxylation, decarboxylation, substitution steps previously described in the context of Reaction Scheme A to afford the corresponding exo-derivatives 9,10, and 11.

Included among the compounds of this invention are:
3-(2,3,4,5,6-pentafluorophenoxy)-3-(4-methylphenyl)-8-azabicyclo[3.2.1]octane;
8-cyano-3-(2,3,4,5,6-pentafluorophenoxy)-3-phenyl-8-azabicyclo[3.2.1]octane;
8-cyclopropylmethyl-3-(2,3,4,5,6-pentafluorophenoxy)-8-azabicyclo[3.2.1]octane;
3-(2,3,4,5,6-pentaflurophenoxy)-8-[3-(3,5-difluorophenyl)propyl]-8-azabicyclo[3.2.1]octane;
3-(2,3,4,5,6-pentafluorophenoxy)-8-methoxycarbonyl-8-azabicyclo[3.2.1]octane;
8-benzylcarbonyl-3-(2,3,4,5,6-pentafluorophenoxy)-8-azabicyclo[3.2.1]octane;
3-(2,3,4,5,6-pentafluorophenoxy)-3-(4-trifluoromethylphenyl)-8-thioformyl-8-azabicyclo[3.2.1]octane;
3-(2,3,4,5,6-pentafluorophenoxy)-8-thioacetyl-8-azabicyclo[3.2.1]octane;
3-(2,3,4,5,6-pentafluorophenoxy)-8-(methoxythiocarbonyl)-8-azabicyclo[3.2.1]octane;
3-(2,3,4,5,6-pentafluorophenoxy)-8-benzyl-8-azabicyclo[3.2.1]octane;
3-(2,3,4,5,6-pentafluorophenoxy)-8-[(N-phenylamino)carbonyl]-8-azabicyclo[3.2.1]octane;
3-(2,3,4,5,6-pentafluorophenoxy)-8-[(N,N-dimethylamino)carbonyl]-8-azabicyclo[3.2.1]octane;
8-cyano-3-(2,3,4,5,6-pentafluorophenoxy)-8-azabicyclo[3.2.1]octane;
8-formyl-3-(2,3,4,5,6-pentafluorophenoxy)-3-phenyl-8-azabicyclo[3.2.1]octane;

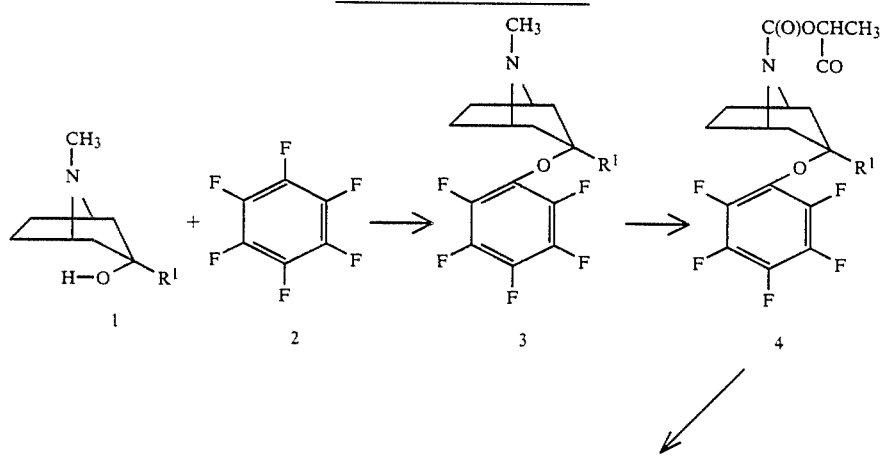

REACTION SCHEME A

-continued
REACTION SCHEME A

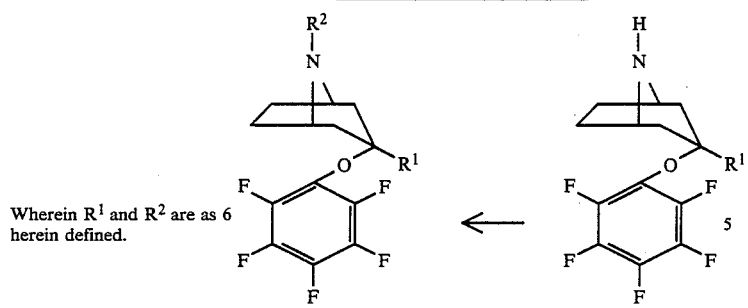

Wherein $R^1$ and $R^2$ are as herein defined.

REACTION SCHEME B

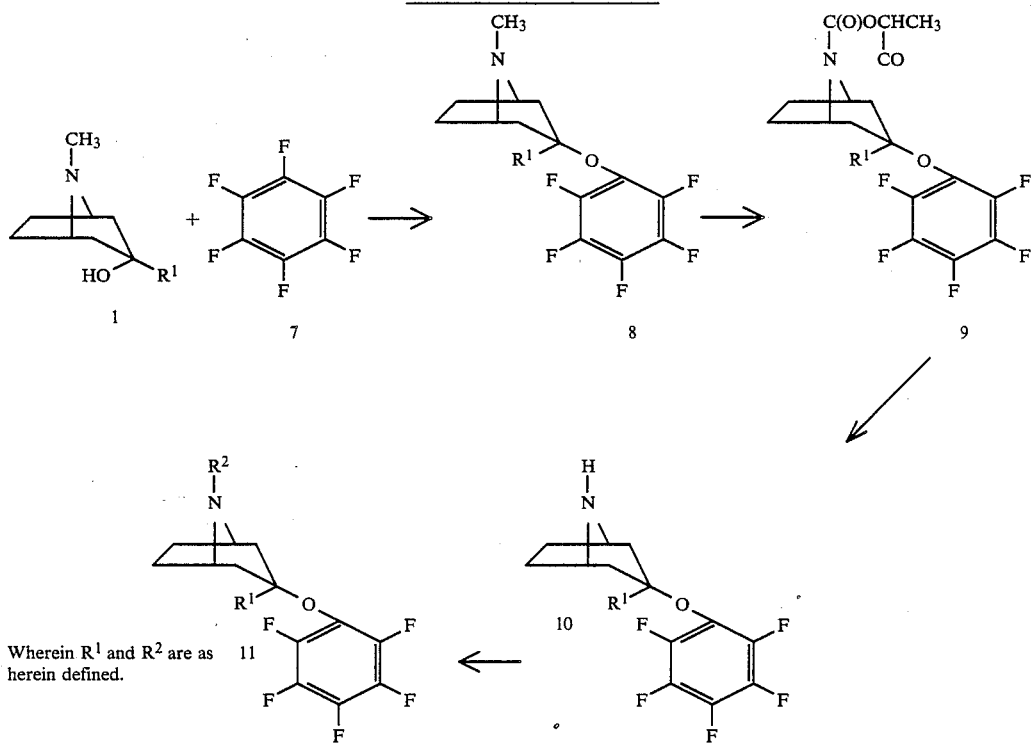

Wherein $R^1$ and $R^2$ are as herein defined.

3-(2,3,4,5,6-pentafluorophenoxy)-3-(4-methoxyphenyl)-8-thioacetyl-8-azabicyclo[3.2.1]octane;

8-(2-aminoethyl)-3-(2,3,4,5,6-pentafluorophenoxy)-8-azabicyclo[3.2.1]octane;

8-benzylthiocarbonyl-3-(2,3,4,5,6-pentafluorophenoxy)-8-aza bicyclo[3.2.1]octane;

8-aminocarbonyl-3-(2,3,4,5,6-pentafluorophenoxy)-3-phenyl-8-azabicyclo[3.2.1]octane;

8-[(N,N-dimethylamino)thiocarbonyl]-3-(2,3,4,5,6-pentafluorophenoxy)-8-azabicyclo[3.2.1]octane;

8-aminothiocarbonyl-3-(2,3,4,5,6-pentafluorophenoxy)-8-azabicyclo[3.2.1]octane;

8-(1-methylpropyl)-3-(2,3,4,5,6-pentafluorophenoxy)-8-azabicyclo[3.2.1]octane;

3-(2,3,4,5,6-pentafluorophenoxy)-8-{4-[1-(4-(2-methoxyphenyl)piperazin-1-yl)]-2-butynyl}-8-azabicyclo[3.2.1]octane;

3-(2,3,4,5,6-pentaflurophenoxy)-8-[3-(N,N-dimethylamino)propyl]-8-azabicyclo[3.2.1]octane;

8-[(N-phenylamino)thiocarbonyl]-3-(2,3,4,5,6-pentafluorophenoxy)-8-azabicyclo[3.2.1]octane;

8-(4-aminobutyl)-3-(2,3,4,5,6-pentafluorophenoxy)-8-azabicyclo[3.2.1]octane;

3-(2,3,4,5,6-pentafluorophenoxy)-8-[3-(N-methylamino)propyl]-8-azabicyclo[3.2.1]octane;

3-(2,3,4,5,6-pentafluorophenoxy)-3-(3,5-dimethylphenyl)-8-thioacetyl-8-azabicyclo[3.2.1]octane; and 3-phenyl-3-(2,3,4,5,6-pentafluorophenoxy)-8-thioformyl-8-azabicyclo[3.2.1]octane.

The compounds of this invention are useful as analgesic agents due to their ability to alleviate pain in mammals. The procedure employed to determine analgetic utility is a modification of the phenyl-p-benzoquinone writhing assay in mice, a standard assay for analgesia [Proc. Soc. Exptl. Bio. Med., 95, 729 (1957)]. Pursuant to the modified procedure phenyl-p-benzoquinone (Eastman, 12.5 mg) is dissolved in 5 ml of 95% ethanol and the solution is diluted tc a total volume of 100 ml with distilled water. The solution is administered to the subject mice intraperitoneally at a dose of 10 ml per kg of body weight. A characteristic "writhe" an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously (s.c.) or orally (p.o.) at 15, 30, 45 and 60 minutes prior to administration of the phenyl-p-quinone. A control group (2 animals per group) receive an equal volume of the vehicle. After the administration of the phenyl-p-quinone, the mice are place separately in one liter beakers, and after five minutes, are observed for ten minutes. The number of writhes for each animal is recorded. The following formula is used to compute the percent inhibition:

$$\frac{x \text{ Writhes in Control Group} - x \text{ Writhes in Drug Group}}{x \text{ Writhes in Control Group}} \times 100$$

The time period with the greatest percent of inhibition is considered the peak time. The results of the phenyl-p-quinone writhing assay for several of the compounds of this invention is provided in Table 1.

TABLE 1

| Compound | Analgesic Activity % Inhibition of writhing at a screening dose of 20 mg/kg, s.c. |
|---|---|
| exo-3-(2,3,4,5,6-pentafluorophenoxy)-8-methyl-8-azabicyclo[3.2.1]octane hydrochloride | 43% |
| exo-8-(aminocarbonyl)-3-(2,3,4,5,6-pentafluorophenoxy)-8-azabicyclo[3.2.1]octane | 32% |
| exo-3-(2,3,4,5,6-pentafluorophenoxy)-8-(N,N-dimethylaminocarbonyl)-8-azabicyclo[3.2.1]octane | 39% |
| exo-8-[3-(6-fluoro-1,2-benzisoxazol-3-yl)propyl]-3-(2,3,4,5,6-pentafluorophenoxy)-8-azabicyclo[3.2.1]octane hydrochloride | 49% |
| endo-3-(2,3,4,5,6-pentafluorophenoxy)-8-methyl-8-azabicyclo[3.2.1]octane oxalate | 49% |
| endo-8-[3-(6-fluoro-1,2-benzisoxazol-3-yl)propyl]-3-(2,3,4,5,6-pentafluorophenoxy)-8-azabicyclo[3.2.1]octane hydrochloride | 45% |
| endo-8-aminocarbonyl-3-(2,3,4,5,6-pentafluorophenoxy)-8-azabicyclo[3.2.1]octane | 38% |
| endo-3-(2,3,4,5,6-pentafluorophenoxy)-8-[(5,6-dimethoxy-1,2-benzisoxazol-3-yl)propyl]-8-azabicyclo[3.2.1]octane hydrochloride | 37% |
| endo-3-(2,3,4,5,6-pentafluorophenoxy)-8-[3-[4-(2-methoxyphenyl)-piperazin-1-yl]propyl]-8-azabicyclo[3.2.1]octane | 55% |
| endo-3-(2,3,4,5,6-pentafluorophenoxy)-8-methyl-3-phenyl-8-azabicyclo[3.2.1]octane hydrochloride | 42% |
| endo-3-(2,3,4,5,6-pentafluorophenoxy)-8-[3-(2-methylindol-3-yl)propyl]-8-azabicyclo[3.2.1]octane hydrochloride | 39% |
| exo-3-(2,3,4,5,6-pentafluorophenoxy)-8-]3-(2-methylindol-3-yl)propyl]-8-azabicyclo[3.2.1]octane hydrochloride | 42% |

TABLE 1-continued

| Compound | Analgesic Activity % Inhibition of writhing at a screening dose of 20 mg/kg, s.c. |
|---|---|
| Asprin | $ED_{50} = 32.8^1$ |

[1] Calculated dosage at which a 50% inhibition of writhing is achieved.

Analgesia production is achieved when the 3-(2,3,4,5,6-pentafluorophenoxy)-8-azabicycl[3.2.1]octanes of this invention are administered to a subject requiring such treatment as an effective oral, parenteral or intravenous dose of from 0.1 to 50 mg/kg of body weight per day.

The compounds of this invention are also useful as anticonvulsants due to their anticonvulsant activity in mammals. Anticonvulsant activity is measured in male mice using the supramaximal electroshock (SES) assay described in *Arch. Int. Pharmacodyn.* 92, pp. 97–107, (1952) and the metrazol lethality assay (MTZ) described in *J. Pharmacol. Exp. Ther.*, 81, 402 (1944).

Groups of male mice (Charles River, CD-1) weighing 18 to 30 g are employed in the SES assay. Test compounds are dissolved in distilled water, or if insoluble, suspended in water containing one drop of a surfactant, such as Tween-80. Test compounds are generally administered intraperitoneally at a dose of 10 ml of solution, or suspension, per kg of animal body weight. The output terminals of an A.C. shocker, which delivers 206 volts rms for 300 msec, are placed across the animals' eyes, an electrode paste coating assuring contact of the terminals with the eyes. The test compound is administered and thereafter the subject animals are shocked.

A test compound is considered to give protection if the mouse does not exhibit extensor tonus. Protection is expressed as normalized percent inhibition relative to vehicle control.

normalized % inhibition =

$$\frac{\left[\frac{\# Rx \text{ Protected} - \# \text{ Control Protected}}{\# Rx \text{ Tested} - \# \text{ Control Tested}}\right]}{1 - \left[\frac{\# \text{ Control Protected}}{\# \text{ Control Tested}}\right]} \times 100$$

A time response is carried out using 6 animals per group. Animals are tested at 30, 60 and 120 minutes post drug. Additional time periods are tested if indicated by previous tests. A dose range determination is generally reserved for those compounds which inhibit convulsions by greater than about 45–55% at the screening dose employed at the time the test was performed. When the peak activity time has been determined, a dose response is initiated, using 10 animals per group at that time period.

Groups of male mice (Charles River, CD-1), weighing 18 to 30 grams are employed in the Metrazol lethality assay. Test compounds are dissolved in distilled water or if insoluble, suspended in water, to which a surfactant, such as Tween-80 is added. The test compounds are administered orally, the administered dose being dissolved or suspended in 10 ml of solution or suspension per kg of animal body weight. Control animals (2 mice/group) receive water or water and Tween-80, i.e., the vehicle for administration of the test compound. Metrazol (pentylenetetrazol) is dissolved in water (concentration 225 mg of Metrazol/10 ml of solution), and the solution is administered subcutaneously to groups of five animals each at one or more time intervals of 15, 30, 60, 90, or 120 minutes after administration of the test compound. The number of animal alive 15 minutes after treatment with Metrazol is determined and recorded. The following formula is employed to calculate the percent protection against Metrazol lethality.

$$\% \text{ protection} = \frac{\text{number of surviving mice}}{\text{number of treated mice}} \times 100$$

A dose range determination is performed by substantially the same procedure as the time response determination. In the dose range determination, five groups of 10 animals per group are employed. This determination is generally reserved for those compounds which protect against lethality by greater than 70% at the screening dose employed.

The anticonvulsant activity of several of the compounds of this invention as per the SES and MTZ assay procedures is provided in Table 2.

TABLE 2

| Compound | Anticonvulsant Activity | |
|---|---|---|
| | MTZ ED$_{50}$ mg/kg p.o. | SES ED$_{50}$ mg/kg i.p. |
| exo-8-acetyl-3-(2,3,4,5,6-pentafluorophenoxy)-8-azabicyclo[3.2.1]octane | 41.9 | |
| endo-8-aminocarbonyl-3-(2,3,4,5,6-pentafluorophenoxy)-8-azabicyclo[3.2.1]octane | 12.7 | 25.2 |
| endo-8-acetyl-3-(2,3,4,5,6-pentafluorophenoxy)-8-azabicyclo[3.2.1]octane | | 35.1 |
| phenobarbital (standard) | 16.9 | 8.4 |

Anticonvulsant activity is achieved when the compounds of this invention are administered to a subject requiring such treatment at an effective oral, parental or intravenous dose of from 10 to 100 mg/kg of body weight per day.

The compounds of this invention are also useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals is treated orally for three days with the test compound in relation to a control group of the same number. The drop in blood pressure is measured on the third day following administration. The antihypertensive activities of representative compounds, expressed as a decrease in mean arterial blood pressure (in mm Hg), are given in Table 3 along with the activity of a standard compound.

TABLE 3

| Antihypertensive Activity SHR | |
|---|---|
| Compound | mm dec. in BP at 50 mg/kg p.o. |
| exo-8-[3-(6-fluoro-1,2,-benzisoxazol-3-yl)-propyl]-3-(2,3,4,5,6-pentafluorophenoxy)-8-azabicyclo[3.2.1]octane hydrochloride | 48 mm |

TABLE 3-continued

| Antihypertensive Activity SHR | |
|---|---|
| Compound | mm dec. in BP at 50 mg/kg p.o. |
| guanethidine (standard) | 20 mm |

Antihypertensive activity is achieved when the compounds of this invention are administered to a subject requiring such treatment at an effective oral, parental or intravenous dose of from 5 to 50 mg/kg of body weight per day.

The compounds of this invention are also useful as antidepressants by virtue of their ability to elicit an antidepressant response in mammals. Antidepressant activity is determined by the L-5-hydroxytryptophan potentiation assay in rats described in *Brit. J. Pharmacol.*, 20, pp. 106–120 (1963) and *J. Med. Chem.*, 24, 74 (1980).

Groups of six male Wistar rats (150–200 grams each) are used in this assay. Pursuant to this procedure pargyline hydrochloride is prepared and administered four hours before testing by subcutaneous injection at 75 mg/kg in 1% saline and at dosage volume of 1.0 ml/kg. Thirty minutes before testing, drugs are prepared and dosed using distilled water and, if insoluble, a suitable surfactant is added. Control groups receive vehicle. Drugs are routinely administered intraperitoneally at a dosage volume of 10 ml/kg. L-5-hydroxytryptophan (5-HTP) is prepared at 1.0 mg/kg in distilled water and is administered intraperioneally in volumes proportional to 10 ml/kg. Drugs are administered in a randomized manner and 15 minutes post 5-HTP treatment, the animals are observed for 15 minutes.

A compound is considered to potentiate 5-HTP activity if the animals exhibit continuous forelimb clonus. Potentiation is expressed as normalized percent potentiation relative to vehicle control.

The antidepressant activity of representative compounds is provided in Table 4.

TABLE 4

| Compound | Antidepressant Activity 5-HTP Potentiation ED$_{50}$ mg/kg i.p. |
|---|---|
| exo-3-(2,3,4,5,6-pentafluro-phenoxy)-8-methyl-8-azabicycl[3.2.1]octane hydrochloride | 13.4 |
| exo-3-(2,3,4,5,6-pentafluorophenoxy)-8-aza bicyclo[3.2.1]octane | 8.4 |
| endo-3-(2,3,4,5,6-pentafluorophenoxy)-8-methyl-8-azabicyclo[3.2.1]octane | 16.2 |
| endo-3-(2,3,4,5,6-pentafluorophenoxy)-8-azabicyclo[3.2.1]octane hydrochloride | 15.6 |
| endo-3-(2,3,4,5,6-pentafluorophenoxy)-8-[(5,6-dimethoxy-1,2-benzisoxazol-3-yl)propyl]-8-azabicyclo[3.2.1]octane hydrochloride | 21.1 |
| endo-3-(2,3,4,5,6-pentafluorophenoxy)-8-(dimethylphosphinyl-methyl)-8-azabicyclo[3.2.1]octane | 10.8 |
| amitriptyline (standard) | 7.1 |

Antidepressant activity is achieved when the compounds of this invention are administered to a subject requiring such treatment at an effective oral, parental or intravenous dose of from 10 to 100 mg/kg of body weight per day.

It is to be understood, however, that the dosages set forth above with respect to analgesic, anticonvulsant, antidepressant, and antihypertensive activity for any particular subject should be adjusted according to the individual need and the professional judgment of the person administering or supervising the administration of the aforesaid compound. It is further understood that the dosages set forth herein are exemplary only and that they do not, to any extent, limit the scope or practice of the invention.

Effective amounts of the compounds of the present invention may be administered to a subject by any one of various methods, for example, orally as in capsules or tablets, parenterally in the form of sterile solutions or suspensions, and in some cases intravenously in the form of sterile solutions. Compounds of this invention, while effective themselves, may be formulated and administered in the form of their pharmaceutically acceptable acid addition salts for purposes of stability, convenience, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, carboxysuccinic acid, citric acid and the like.

Effective quanitites of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; and excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit is a capsule, it may contain, in addition to materials of the preceeding type, a liquid carrier such as a fatty oil. Other dosage unit forms may contain other various materials which modify the physical form of the dosage unit such as, for example, coatings. Thus, tablets or pills may be coated with sugar, shellac, or other enteric coating agents. A syrup may contain, in addition to the active compounds, sucrose and/or flavorings. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multipl dose vials made of glass or plastic.

EXAMPLES

The following Examples are for illustrative purposes only and are not to be construed as limiting the invention.

EXAMPLE 1
(ENDO)-3-(2,3,4,5,6-PENTAFLUOROPHENOXY)-8-METHYL-8-AZABICYCLO[3.2.1]OCTANE OXALATE

To a suspension of sodium hydride (60% in oil, 1.6 g, treated with hexanes) in 10 ml of dry dimethylformamide, was added a solution of 4.5 g of 3-hydroxy-8-methyl-8-azabicyclo[3.2.1]octane in 50 ml of dimethylformamide. The mixture was heated at 60° C. for 30 minutes, cooled to 5° C., and treated with a chilled (−78° C.) solution of 11.6 ml of hexafluorobenzene in 25 ml of dry dimethylformamide. After stirring at −78° C. for 1 hour, the mixture was poured into 200 ml of water, stirred for 5 minutes, then extracted with ethyl acetate. The organic layer was washed with water followed by a saturated sodium chloride solution, dried over anhydrous magnesium sulfate, filtered, and evaporated to an oil. Purification of the oil was accomplished by means of high pressure liquid chromatography (silica gel; elution with 20% methanol/dichloromethane) to afford 4.6 g of (endo)-3-(2,3,4,5,6-pentafluorophenoxy)-8-methyl-8-azabicyclo[3.2.1]octane, m.p. 42°–43° C. Treatment of a 2.5 g sample of this product with ethereal oxalic acid afforded 2.7 g of (endo)-3-(2,3,4,5,6-pentafluorophenoxy)-8-methyl-8-azabicyclo[3.2.1]octane, m.p. 170° C. (dec).

| ANALYSIS: | | | |
|---|---|---|---|
| Calculated for $C_{14}H_{14}F_5NO.(Co_2H)_2$: | 48.37% C | 4.06% H | 3.53% N |
| Found: | 48.14% C | 4.19% H | 3.46% N |

EXAMPLE 2
(ENDO)-8-(1CHLOROETHOXYCARBONYL)-3-(2,3,4,5,6-PENTAFLUOROPHENOXY-8-AZABICYCLO[3.2.1]OCTANE

To a solution of 2.0 g of endo-3-(2,3,4,5,6-pentafluorophenoxy)-8-methyl-8-azabicyclo[3.2.1]octane in 30 ml of dichloroethane was added 0.4 ml of triethylamine, followed by a solution of 0.8 ml of α-chloroethyl chloroformate in 10 ml of dichloroethane. After stirring at 80° C. for two hours, the mixture was cooled, diluted with 100 ml of diethyl ether, washed with water, then dried over anhydrous magnesium sulfate. After filtering, the solvents were evaporated to afford 2.2 g of endo-8-(1-chloroethoxycarbonyl)-3-(2,3,4,5,6-pentafluorophenoxy)-8-azabicyclo[3.2.1]octane as an oil. No further purification was attempted.

EXAMPLE 3
(ENDO)-3-(2,3,4,5,6-PENTAFLUOROPHENOXY)-8-AZABICYCLO[3.2.1]OCTANE HYDROCHLORIDE

A solution of 2.2 g of (endo)-8-(1-chloroethoxycarbonyl)-3-(2,3,4,5,6-pentafluorophenoxy)-8-azabicyclo[3.2.1]octane in 30 ml of methanol was refluxed at 80° C. for 2 hours. Evaporation of the solvent afforded a solid which was triturated with dietheyl ether, collected, and dried to afford 2.1 g (95%) of (endo)-3-(2,3,4,5,6-pentafluorophenoxy)-8-azabicyclo[3.2.1]octane hydrochloride, m.p. 240° C. (dec).

| ANALYSIS: | | | |
|---|---|---|---|
| Calculated for $C_{13}H_{12}F_5NO.HCL$: | 47.36% C | 3.97% H | 4.25% N |
| Found: | 47.21% C | 3.93% H | 4.31% N |

EXAMPLE 4
(ENDO)-8-FORMYL-3-(2,3,4,5,6-PENTAFLUOROPHENOXY)-8-AZABICYCLO[3.2.1]OCTANE

A mixture of 3.5 ml of acetic anhydride and 1.5 ml of formic acid were heated at 65° C. for 1 hour, cooled to ice bath temperature, and treated with 3.5 g of (endo)-3-(2,3,4,5,6-pentafluorophenoxy)-8-azabicyclo[3.2.1]octane. After stirring at ambient temperature for 3 hours, the reaction mixture was poured into water, treated with sodium bicarbonate, and extracted with ethyl acetate. The organic layer was washed with water followed by a saturated sodium chloride solution, dried over anhydrous magnesium sulfate, filtered, and concentrated to an oil. Purification of the oil was accomplished by means of high pressure liquid chromatography (silica gel; elution with ethyl acetate) to afford 3.44 g (89.4%) of (endo)-8-formyl-3-(2,3,4,5,6-pentafluorophenoxy)-8-azabicyclo[3.2.1]octane, m.p. 78°-80° C.

| ANALYSIS: | | | |
|---|---|---|---|
| Calculated for $C_{14}H_{12}F_5NO_2$: | 52.34% C | 3.74% H | 436% N |
| Found: | 52.33% C | 3.56% H | 4.19% N |

EXAMPLE 5
(ENDO)-8-ACETYL-3-(2,3,4,5,6-PENTAFLUOROPHENOXY)-8-AZABICYCLO[3.2.1]OCTANE

A solution of 1.84 ml of triethylamine and 3.5 g of (endo)-3-(2,3,4,5,6-pentafluorophenoxy)-8-azabicyclo[3.2.1]octane in 30 ml of dichloromethane was treated, dropwise, with a solution of 1.03 g of acetyl chloride in 20 ml of dichloromethane. After stirring at ambient temperature for 4 hours, the reaction mixture was washed with water followed by a saturated sodium chloride solution, dried over anhydrous magnesium sulfate, filtered and concentrated to an oil. The oil was purified by means of high pressure liquid chromatography (silica gel; elution with ethyl acetate) to afford 3.3 g (82.1%) of (endo)-8-acetyl-3-(2,3,4,5,6-pentafluorophenoxy)-8-azabicyclo[3.2.1]octane, m.p. 75°-78° C.

| ANALYSIS: | | | |
|---|---|---|---|
| Calculated for $C_{12}H_{14}F_5NO_2$: | 53.73% C | 4.18% H | 4.18% N |
| Found: | 53.82% C | 4.06% H | 4.30% N |

EXAMPLE 6
(ENDO)-8-AMINOCARBONYL-3-(2,3,4,5,6-PENTAFLUOROPHENOXY)-8-AZABICYCLO[3.2.1]OCTANE

A stirred solution of 4.0 g of (endo)-3-(2,3,4,5,6-pentafluorophenoxy)-8-azabicyclo[3.2.1]octane in 50 ml of 95% ethanol was treated with 2.10 g of nitrourea and heated at 70° C. for 1.5 hours. The reaction mixture was then poured into water and extracted with ethyl acetate. The organic layer was washed with water followed by a saturated sodium chloride solution, dried over anhydrous magnesium sulfate, filtered, and concentrated. The concentrate was purified by means of high pressure liquid chromatography to afford 2.93 g (72.7%) of (endo)-8-aminocarbonyl-3-(2,3,4,5,6-pentafluorophenoxy)-8-azabicyclo[3.2.1]octane, m.p. 172°-175° C.

| ANALYSIS: | | | |
|---|---|---|---|
| Calculated for $C_{14}H_{13}F_5N_2O_2$: | 50.00% C | 3.87% H | 8.33% N |
| Found: | 50.02% C | 3.86% H | 8.32% N |

EXAMPLE 7
(ENDO)-3-(2,3,4,5,6-PENTAFLUOROPHENOXY)-8-[(N-METHYLAMINO)CARBONYL]-8-AZABICYCLO[3.2.1]OCTANE

A solution of 3.5 g of (endo)-3-(2,3,4,5,6-pentafluorophenoxy)-8-azabicyclo[3.2.1]octane in 40 ml of benzene was treated with a solution of 1 ml of methylisocyanate in 10 ml of benzene and stirred at ambient temperature for 5 hours. Evaporation of the solvent afforded a solid which was purified by means of high pressure liquid chromatography (silica gel; elution with ethyl acetate/dichloromethane 3:2) to yield 3.5 g (83% of (endo)-3-(2,3,4,5,6-pentafluorophenoxy)-8-[(N-methylamino)carbonyl]-8-azabicyclo[3.2.1]octane, m.p. 165°-166° C.

| ANALYSIS: | | | |
|---|---|---|---|
| Calculated for $C_{15}H_{15}F_5N_2O_2$: | 51.43% C | 4.32% H | 8.00% N |
| Found: | 51.41% C | 4.20% H | 8.10% N |

EXAMPLE 8
(ENDO)-3-(2,3,4,5,6-PENTAFLUOROPHENOXY)-8-[(N,N-DIMETHYLAMINO)CARBONYL]-8-AZABICYCLO[3.2.1]OCTANE

A solution of 5 g of potassium carbonate in 50 ml of water was combined with a solution of 3.5 g of (endo)-3-(2,3,4,5,6-pentafluorophenoxy)-8-azabicyclo[3.2.1]octane and the resultant mixture treated, dropwise, with a solution of 2.5 ml of dimethylcarbamyl chloride in 10 ml of chloroform. After stirring at ambient temperature for 8 hours the organic layer was separated, washed with water followed by a saturated solution of sodium chloride, dried over anhydrous magnesium sulfate, filtered and concentrated to an oil. High pressure liquid chromatography of the oil yielded 2.5 g (57.2%) of (endo)-3-

(2,3,4,5,6-pentafluorophenoxy)-8-[(N,N-dimethylamino)arbonyl]-8-azabicyclo[3.2.1]octane, m.p. 63°–66° C.

| ANALYSIS: | | | |
|---|---|---|---|
| Calculated for $C_{16}H_{17}F_5N_2O_2$: | 52.75% C | 4.67% H | 7.69% N |
| Found: | 52.56% C | 4.65% H | 7.83% N |

EXAMPLE 9
(ENDO)-3-(2,3,4,5,6-PENTAFLUOROPHENOXY)-8-METHYL-3-PHENYL-8-AZABICYCLO[3.2.1]OCTANE HYDROCHLORIDE

A suspension of sodium hydride (60% in oil, 2.0 g, washed with hexanes) in 20 ml of dry dimethylformamide was treated with a suspension of 10 g of 3-hydroxy-8-methyl-3-phenyl-8-azabicyclo[3.2.1]octane in 100 ml of dry dimethylformamide. The reaction mixture was then heated at 80° C. for 1 hour, cooled to 5° C., and treated with a chilled (−78° C.) solution of 7 ml of hexafluorobenzene in 35 ml of dry dimethylformamide. After stirring at −78° C. for 1 hour, the mixture was poured into 200 ml of water, stirred for 5 minutes and extracted with ethyl acetate. The organic layer was washed with water followed by a saturated solution of sodium chloride, dried over anhydrous magnesium sulfate, filtered, and evaporated to an oil. Purification of the oil was accomplished by means of high pressure liquid chromatography (silica gel; elution with 20% methanol/dimethylformamide) to yield 6.8 g (39%) of (endo)-3-(2,3,4,5,6-pentafluorophenoxy)-8-methyl-3-phenyl-8-azabicyclo[3.2.1]octane as an oil.

A 3.0 g sample of the oil was treated with ethereal hydrogen chloride to afford 2.7 g of (endo)-3-(2,3,4,5,6-pentafluorophenoxy)-8-methyl-3-phenyl-8-azabicyclo[3.2.1]octane hydrochloride, m.p. 175 (dec).

| ANALYSIS: | | | |
|---|---|---|---|
| Calculated for $C_{20}H_{18}F_5NO\cdot HCl$: | 57.21% C | 4.56% H | 3.34% N |
| Found: | 57.07% C | 4.67% H | 3.38% N |

EXAMPLE 10
(ENDO)-8-[3-(6-FLUORO-1,2-BENZISOXAZOL-3-YL)PROPYL]-3-(2,3,4,5,6-PENTAFLUOROPHENOXY)-8-AZABICYCLO[3.2.1]OCTANE HYDROCHLORIDE

A mixture of 4.0 g of (endo)-3-(2,3,4,5,6-pentafluorophenoxy)-8-azabicyclo[3.2.1]octane, 10 g of potassium carbonate, 0.1 g of potassium iodide, and 75 ml of dimethylformamide was stirred at 80° C. for 8 hours. The reaction mixture was then cooled, poured into 200 ml of water, stirred for 5 minutes and extracted with ethyl acetate. The organic layer was washed with water followed by a saturated sodium chloride solution, dried over anhydrous magnesium sulfate, filtered, and evaporated. Purification of the concentrate was accomplished by means of high pressure liquid chromatography (silica gel; elution with ethyl acetate) to afford 3.5 g of (endo)-8-[3-(6-fluoro-1,2-benzisoxazol-3-yl)propyl]-3-(2,3,4,5,6-pentafluorophenoxy)-8-azabicyclo[3.2.1]octane as an oil. Treatment of the oil with ethereal hydrogen chloride afforded 3.2 g (45%) of the corresponding hydrochloride salt, m.p. 205° C. (dec).

| ANALYSIS: | | | |
|---|---|---|---|
| Calculated for $C_{23}H_{20}F_6N_2O_2\cdot HCL$ | 54.50% C | 4.18% H | 5.53% N |
| Found: | 54.37% C | 4.16% H | 5.53% N |

EXAMPLE 11
(ENDO)-3-(2,3,4,5,6-PENTAFLUOROPHENOXY)-8-[3-(2-METHYLINDOL-3-YL)PROPYL]-8-AZABICYCLO[3.2.1]OCTANE HYDROCHLORIDE

A mixture of 3.5 g of (endo)-3-(2,3,4,5,6-pentafluorophenoxy)-8-azabicyclo[3.2.1]octane, 4.0 g of 3-(2-methylindol-3-yl)propyl phenyl sulfonate, 10 g of potassium carbonate, and 80 ml of dry dimethylformamide was stirred at 85° C. for 5 hours. The reaction mixture was then poured into 200 ml of water, stirred for 5 minutes, and extracted with ethyl acetate. The organic layer was washed with water followed by a saturated solution of sodium chloride, dried over anydrous magnesium sulfate, filtered, and evaporated. The concentrate was purified by means of high pressure liquid chromatography to afford 4 g of (endo)-3-(2,3,4,5,6-pentafluorophenoxy)-8-[3-(2-methylindol-3-yl)propyl]-8-azabicyclo[3.2.1]octane as an oil. Treatment of the oil with ethereal hydrogen chloride afforded the corresponding hydrochloride salt, m.p. 213° C. (dec).

| ANALYSIS: | | | |
|---|---|---|---|
| Calculated for $C_{25}H_{25}F_5N_2O\cdot HCL$: | 59.94% C | 5.23% H | 5.59% N |
| Found: | 60.14% C | 5.25% H | 5.58% N |

EXAMPLE 12
(ENDO)-3-(2,3,4,5,6-PENTAFLUOROPHENOXY)-8-[(5,6-DIMETHOXY-1,2-BENZISOXAZOL-3-YL)PROPYL]8-AZABICYCLO[3.2.1]OCTANE HYDROCHLORIDE

A mixture of 4.0 g of (endo)-3-(2,3,4,5,6-pentafluorophenoxy)-8-azabicyclo[3.2.1]octane, 5.3 g of 3-(3-chloropropyl)-5,6-dimethoxy-1,2-benzisoxazole, 10 g of potassium carbonate, 0.01 g of potassium iodide, and 80 ml of dry dimethyl formamide was stirred at 80° C. for four hours.

The reaction mixturea was then cooled, poured into 200 ml of water, stirred for 5 minutes and extracted with ethyl acetate. The organic layer was washed with water followed by a saturated sodium chloride solution, dried over anhydrous magnesium sulfate, filtered and evaporated. The concentrate was purified by means of high pressure liquid chromatography (silica gel; elution with ethyl acetate) to yield 3.0 g of (endo)-3-(2,3,4,5,6-pentafluorophenoxy)-8-[(5,6-dimethoxy-1,2-benzisoxazol-3-ly)propyl]-8-azabicyclo[3.2.1]octane as an oil.

Treatment of the oil with ethereal hydrogen chloride afforded 3.2 g (42%) of the corresponding hydrochloride salt, m.p. 222° C. (dec).

| ANALYSIS: | | | |
|---|---|---|---|
| Calculated for $C_{25}H_{25}F_5N_2O_4\cdot HCL$: | 54.40% C | 4.75% H | 5.08% N |
| Found: | 54.64% C | 4.94% H | 5.29% N |

EXAMPLE 13
(ENDO)-3-(2,3,4,5,6-PENTAFLUOROPHENOXY)-8-[3-[4-(2-METHOXYPHENYL)-PIPERAZIN-1-YL]PROPYL]-8-AZABICYCLO[3.2.1]OCTANE

A mixture of 6.0 g of (endo)-3-(2,3,4,5,6-pentafluorophenoxy)-8-azabicyclo[3.2.1]octane, 6.98 g of 1-(2-methoxyphenyl)-4-(3-chloropropyl)piperazine, 5 g of potassium carbonate, and 100 ml of dimethylformamide was stirred at 70° C. for 5 hours. The reaction mixture was then cooled and filtered. The filtrate was poured into water and extracted with ethyl acetate. The organic layer was washed with water followed by a saturated sodium chloride solution, dried over anhydrous magnesium sulfate, filtered, and evaporated. The concentrate was purified by high pressure liquid chromatography (silica gel; elution with dichloromethane) to yield 3.5 g (33.3%) of (endo)-3-(2,3,4,5,6-pentafluorophenoxy)-8-[3-[4-(2-methoxyphenyl)-piperazin-1-yl]propyl]-8-azabicyclo[3.2.1]octane, m.p. 75°–78° C.

| ANALYSIS: | | | |
|---|---|---|---|
| Calculated for $C_{27}H_{32}F_5N_3O_2$: | 61.71% C | 6.10% H | 8.00% N |
| Found: | 61.38% C | 6.09% H | 7.79% N |

EXAMPLE 14
(ENDO)-3-(2,3,4,5,6-PENTAFLUOROPHENOXY)-8-[4-(2-OXOPYRROLIDIN-1-YL)-2-BUTYNYL]-8-AZABICYCLO[3.2.1]OCTANE OXALATE

A mixture of 3.5 g of (endo)-3-(2,3,4,5,6-pentafluorophenoxy)-8-azabicyclo[3.2.1]octane, 2 g of paraformaldehyde, 1.9 g of 1-(2-butynyl)pyrrolidin-2-one, 0.1 g of copper(I) chloride, and 100 ml of p-dioxane was stirred at 100° C. for 2 hours. The reaction mixture was then cooled, diluted with 200 ml of ethyl acetate, and filtered. The filtrate was washed with water followed by a saturated sodium chloride solution, dried over anhydrous magnesium sulfate, filtered, and concentrated. The concentrate was purified by means of high pressure liquid chromatography to yield 5.6 g of (endo)-3-(2,3,4,5,6-pentafluorophenoxy)-8-[4-(2-oxopyrrolidin-1-yl)-2-butynyl]-8-azabicyclo[3.2.1]octane as an oil. Treatment of the oil with ethereal oxalic acid yielded 2.1 g (34%) of the corresponding oxalate salt, m.p. 142° C. (dec).

| ANALYSIS: | | | |
|---|---|---|---|
| Calculated for $C_{21}H_{21}F_5N_2O_2 \cdot (CO_2H)_2$: | 53.28% C | H | 5.40% N |
| Found: | 53.08% C | 4.47% H | 5.43% N |

EXAMPLE 15
(ENDO)-3-(2,3,4,5,6-PENTAFLUOROPHENOXY)-8-[(DIMETHYLPHOSPHINYL)METHYL]-8-AZABICYCLO[3.2.1]OCTANE

A mixture of 5 g of potassium carbonate and 4.0 g of (endo)-3-(2,3,4,5,6-pentafluorophenoxy)-8-azabicyclo[3.2.1]octane in 100 ml of dimethylformamide was treated with 3.54 g of dimethyl phosphinyl methyl chloride and then stirred at 85° C. for thirty hours. The reaction mixture was then cooled and filtered. The filtrate was poured into water and extracted with ethyl acetate. The organic layer was washed with water followed by a saturated sodium chloride solution, dried over anhydrous magnesium sulfate, filtered and concentrated. The residue was purified by means of high pressure liquid chromatography (silica gel; elution with 5% methanol/dichloromethane). Trituration of the resultant solid with diethyl ether afforded 2.63 g (49.1%) of (endo)-3-(2,3,4,5,6-pentafluorophenoxy)-8-[(dimethylphosphinyl)methyl]-8-azabicyclo[3.2.1]octane, m.p. 61°–65° C.

| ANALYSIS: | | | |
|---|---|---|---|
| Calculated for $C_{16}H_{19}F_5NO_2P$: | 50.13% C | 4.96% H | 3.66% N |
| | 50.06% C | 5.01% H | 3.75% N |

EXAMPLE 16
(EXO)-3-(2,3,4,5,6-PENTAFLUOROPHENOXY)-8-METHYL-8-AZABICYCLO[3.2.1]OCTANE HYDROCHLORIDE

A stirred, chilled (ice bath temperature) mixture of 7.63 g of 3-hydroxy-8-methyl-8-azabicycl[3.2.1]octane, 10.00 g of pentafluorophenol, and 15.48 g of triphenylphosphine in 100 ml of benzene was treated, dropwise, with a solution of 9.29 ml of diethyl azodicarboxylate in 30 ml of benzene and stirred at ambient temperature for 24 hours. The reaction mixture was then filtered, and the filtrate evaporated to an oil. Purification of the oil was accomplished by means of high pressure liquid chromatography (silica gel; elution with 10% methano/dichloromethane) to yield 10.98 g of (exo)-3-(2,3,4,5,6-pentafluorophenoxy)-8-methyl-8-azabicyclo[3.2.1]octane. A 9.2 g sample of this product was dissolved in ethyl acetate and treated with ethereal hydrogen chloride to precipitate 2.0 g of the corresponding hydrochloride salt, m.p. 214°–216° C.

| ANALYSIS: | | | |
|---|---|---|---|
| Calculated for $C_{14}H_{14}F_5NO \cdot HCl$: | 48.91% C | 4.37% H | 4.08% N |
| Found: | 49.03% C | 4.26% H | 3.96% N |

EXAMPLE 17
(EXO)-8-(α-CHLOROETHOXYCARBONYL)-3-(2,3,4,5,6-PENTAFLUOROPHENOXY)-8-AZABICYCLO[3.2.1]OCTANE

A chilled (ice bath temperature) solution of 13.81 g of (exo)-3-(2,3,4,5,6-pentafluorophenoxy)-8-methyl-8-azabicyclo[3.2.1]octane and 12.54 ml of triethylamine in 50 ml of dichloroethane was treated dropwise with a solution of 12.87 g of α-chloroethylchloroformate in 20 ml of dichloroethane. After stirring at ice bath temperature for 15 minutes the reaction mixture was heated at 70° C. for 3 hours. The mixture was then diluted with ethyl acetate, washed with water followed by a saturated sodium chloride solution, dried over anhydrous magnesium sulfate, filtered, and concentrated to an oil (16.4 g). A 4.0 g sample of this oil was purified by means of high pressure liquid chromatography (silica gel; elution with dichloromethane) to yield 3.0 g of (exo)-8-(α-chloroethoxycarbonyl)-3-(2,3,4,5,6-pentafluorophenoxy)-8-azabicyclo[3.2.1]octane, m.p. 75°–80° C.

| ANALYSIS: | | | |
|---|---|---|---|
| Calculated for $C_{16}H_{15}ClF_5NO_3$: | 48.06% C | 3.75% H | 3.50% N |

-continued

| ANALYSIS: | | | |
|---|---|---|---|
| Found: | 47.97% C | 3.82% H | 3.43% N |

EXAMPLE 18
(EXO-3-(2,3,4,5,6-PENTAFLUOROPHENOXY)-8-AZABICYCLO[3.2.1]OCTANE

A mixture of 29.70 g of (exo)-8-(α-chloroethoxycarbonyl)-3-(2,3,4,5,6-pentafluorophenoxy)-8-azabicyclo[3.2.1]octane and 100 ml of methanol was refluxed for 1 hour. The reaction mixture was then cooled and concentrated to an oil. The oil was dissolved in water and basified by the addition of an aqueous solution of sodium carbonate. The aqueous layer was extracted with ethyl acetate and the combined organic later was washed with water followed by a saturated sodium chloride solution, dried over anhydrous magnesium sulfate, filtered, and concentrated. Thus, was obtained 20.10 g (92.7%) of (exo)-3-(2,3,4,5,6-pentafluorophenoxy)-8-azabicyclo[3.2.1]octane, m.p. 50°–53° C.

| ANALYSIS: | | | |
|---|---|---|---|
| Calculated for $C_{13}H_{12}F_5NO$: | 53.24% C | 4.10% H | 4.78% N |
| Found: | 52.83% C | 4.00% H | 4.75% N |

EXAMPLE 19
(EXO)-8-FORMYL-3-(2,3,4,5,6-PENTAFLUOROPHENOXY-8-AZABICYCLO[3.2.1]OCTANE

A mixture of 3.5 ml of acetic anhydride and 1.5 ml of formic acid was stirred at 60° C. for 1 hour, cooled, and treated with a solution of 4.0 g of (exo)-3-(2,3,4,5,6-pentafluorophenoxy)-8-azabicyclo[3.2.1]octane in 75 ml of diethyl ether. After stirring at ambient temperature for 3 hours, the reaction mixture was poured into 100 ml of water, treated with sodium bicarbonate, and extracted with ethyl acetate. The organic layer was washed with water followed by a saturated sodium chloride solution, dried over anhydrous magnesium sulfate, filtered, and concentrated. The concentrate was purified by means of high pressure liquid chromatography (silica gel; elution with ethyl acetate) to yield 3.2 g (74%) of (exo)-8-formyl-3-(2,3,4,5,6-pentafluorophenoxy-8-azabicyclo[3.2.1]octane, m.p. 114°–115° C.

| ANALYSIS: | | | |
|---|---|---|---|
| Calculated for $C_{14}H_{12}F_5NO_2$: | 52.34% C | 3.77% H | 4.36% N |
| Found: | 52.39% C | 3.74% H | 4.45% N |

EXAMPLE 20
(EXO)-8-ACETYL-3-(2,3,4,5,6-PENTAFLUOROPHENOXY)-8-AZABICYCLO[3.2.1]OCTANE

A stirred mixture of 3.5 g of (exo)-3-(2,3,4,5,6-pentafluorophenoxy)-8-azabicyclo[3.2.1]octane and 1.84 ml of triethylamine in 20 ml of dichloromethane was treated, dropwise, with a solution of 1.03 g of acetyl chloride in 30 ml of dichloromethane. After stirring at ambient temperature for 2 hours the reaction mixture was washed with water followed by a saturated sodium chloride solution, dried over anhydrous magnesium sulfate, filtered, and concentrated. The concentrate was purified by means of high pressure liquid chromatography (silica gel; elution with ethyl acetate) to yield 3.82 g (95.0%) of (exo)-8-acetyl-3-(2,3,4,5,6-pentafluorophenoxy)-8-azabicyclo[3.2.1]octane, m.p. 104°–106° C.

| ANALYSIS: | | | |
|---|---|---|---|
| Calculated for $C_{15}H_{14}F_5NO_2$: | 53.73% C | 4.18% H | 4.18% N |
| Found: | 53.88% C | 4.26% H | 4.23% N |

EXAMPLE 21
(EXO)-8-(AMINOCARBONYL)-3-(2,3,4,5,6-PENTAFLUORORPHENOXY)-8-AZABICYCLO[3.2.1]OCTANE

A stirred solution of 3.5 g of (exo)-3-(2,3,4,5,6-pentafluorophenoxy)-8-azabicyclo[3.2.1]octane in 50 ml of 95% ethanol was treated with 1.89 g of nitrourea and then stirred at 70° C. for 1.5 hours. The reaction mixture was then poured into water and extracted with ethyl acetate. The organic layer was washed with water followed by a saturated solution of sodium chloride, dried over anhydrous magnesium sulfate, filtered, and concentrated. The concentrate was purified by means of high pressure liquid chromatography (silica gel; elution with ethyl acetate) to yield 2.93 g (72.7%) of (exo)-8-(aminocarbonyl)-3-(2,3,4,5,6-pentafluorophenoxy)-8-azabicyclo[3.2.1]octane, m.p. 172°–175° C.

| ANALYSIS: | | | |
|---|---|---|---|
| Calculated for $C_{14}H_{13}F_5N_2O_2$: | 50.00% C | 3.87% H | 8.33% N |
| Found: | 49.79% C | 3.95% H | 8.23% N |

EXAMPLE 22
(EXO)-3-(2,3,4,5,6-PENTAFLUOROPHENOXY)-8-[(N,N-DIMETHYLAMINO)CARBONYL]-8-AZABICYCLO[3.2.1]OCTANE

A stirred mixture of 5 g of potassium carbonate in 50 ml of water and 3.5 g of (exo)-3-(2,3,4,5,6-pentafluorophenoxy)-8-azabicyclo[3.2.1]octane in 50 ml of chloroform was treated, dropwise, with a solution of 2.5 ml of dimethylcarbamoyl chloride in 20 ml of chloroform and then stirred at ambient temperature for 24 hours. The organic layer was separated, washed with water followed by a saturated sodium chloride solution, dried over anhydrous magnesium sulfate, filtered and concentrated. The concentrate was purified by means of high pressure liquid chromatography (silica gel; elution with ethyl acetate) to yield 3.12 g (71.4%) of (exo)-3-(2,3,4,5,6-pentafluorophenoxy)-8-[(N,N-dimethylamino)carbonyl]8-azabicyclo[3.2.1]octane, m.p. 70°–73° C.

| ANALYSIS: | | | |
|---|---|---|---|
| Calculated for $C_{16}H_{17}F_5N_2O_2$: | 52.75% C | 4.67% H | 7.69% N |
| Found: | 52.70% C | 4.68% H | 7.69% N |

EXAMPLE 23
(EXO)-8-[3-(6-FLUORO-1,2-BENZISOXAZOL-3-YL)PROPYL]-3-(2,3,4,5,6-PENTAFLUOROPHENOXY)-8-AZABICYCLO[3.2.1]OCTANE HYDROCHLORIDE

A mixture of 4.0 g of (exo)-3-(2,3,4,5,6-pentafluorophenoxy)-8-azabicyclo[3.2.1]octane, 5.5 g of 3-(3-chloropropyl)-6-fluoro-1,2-benzisoxazole, 10 g of potassium carbonate, 0.1 g of potassium iodide and 75 ml of dry dimethylformamide was stirred at 80° C. for 7 hours. The reaction mixture was then poured into 200 ml of water, stirred for 5 minutes, and extracted with ethyl acetate. The organic layer was washed with water followed by a saturated sodium chloride solution, dried over anhydrous magnesium sulfate, filtered, and concentrated to an oil. The oil was purified by means of high pressure liquid chromatography (silica gel; elution with ethyl acetate) to yield 3.5 g of (exo)-8-[3-(6-fluoro-1,2-benzisoxazol-3-yl)propyl]-3-(2,3,4,5,6-pentafluorophenoxy)-8-azabicyclo[3.2.1]octane as an oil which solidified upon standing; m.p. 57°–58° C. The solid was dissolved in diethyl ether and treated with ethereal hydrogen chloride to precipitate 3.0 g (44%) of the corresponding hydrochloride salt, m.p. 217° C. (dec).

| ANALYSIS: | | | |
|---|---|---|---|
| Calculated for $C_{23}H_{20}F_5N_2O_2 \cdot$ HCL | 54.50% C | 4.18% H | 5.53% N |
| Found: | 54.14% C | 4.10% H | 5.42% N |

EXAMPLE 24
(EXO)-8-[1-(1,3-DIHYDRO-2-OXO-2H-BENZIMIDAZOL-1-YL)PROPYL]-3-(2,3,4,5,6-PENTAFLUOROPHENOXY)-8-AZABICYCLO[3.2.1]OCTANE

To a mixture of 5 g of sodium bicarbonate, 4.0 g of (exo)-3-(2,3,4,5,6-pentafluorophenoxy)-8-azabicyclo[3.2.1]octane, and 100 ml of dimethylformamide heated to 70° C. was added, portionwise, 5.87 g of 1-(3-chloropropyl)-1,3-dihydro-2-oxo-2H-benzimidazole. After stirring for 6 hours at 70° C. the reaction mixture was cooled and filtered. The filtrate was poured into water and extracted with ethyl acetate. The organic layer was washed with water followed by a saturated sodium chloride solution, dried over anhydrous magnesium sulfate, filtered and concentrated. The concentrate was purified by means of high pressure liquid chromatography (silica gel; elution with 5% methanol/dichloromethane) to yield 3.6 g (55.2%) of (exo)-8-[1-(1,3-dihydro-2-oxo-2H-benzimidazol-1-yl)propyl]-3-(2,3,4,5,6-pentafluorophenoxy)-8-azabicyclo[3.2.1]octane, m.p. 130°–133° C.

| ANALYSIS: | | | |
|---|---|---|---|
| Calculated for $C_{23}H_{21}F_5N_3O_2$: | 59.23% C | 4.51% H | 9.01% N |
| Found: | 58.92% C | 4.77% H | 9.00% N |

EXAMPLE 25
(EXO)-3-(2,3,4,5,6-PENTAFLUOROPHENOXY)-8-[3-[4-(2-METHOXYPHENYL)PIPERAZIN-1-YL]PROPYL]-8-AZABICYCLO[3.2.1]OCTANE DIFUMARATE

To a stirred mixture of 5 g of potassium carbonate and 0.15 g of potassium iodide in 100 ml of dimethylformamide was added 3.8 g of (exo)-3-(2,3,4,5,6-pentafluorophenoxy)-8-azabicyclo[3.2.1]octane followed by a solution of 4.03 g of 1-(3-chloropropyl)-4-(2-methoxyphenyl)piperazine in 20 ml of dimethylformamide. After stirring at 78° C. for 4 hours the reaction mixture was cooled to ambient temperature, poured into water, and extracted with ethyl acetate. The organic layer was washed with water followed by a saturated sodium chloride solution, dried over anhydrous magnesium sulfate, filtered, and concentrated. The concentrate was purified by means of high pressure liquid chromatography (silica gel; elution with 5% methanol/dichloromethane) to yield (exo)-3-(2,3,4,5,6-pentafluorophenoxy)-8-[3-[4-(2-methoxyphenyl)-piperazin-1-yl]propyl]-8-azabicyclo[3.2.1]octane as an oil. The oil was dissolved in isopropanol and acidified with fumaric acid (isopropanol solution) to afford 2.95 g (29.0%) of the corresponding difumarate salt, m.p. 194°–196° C.

| ANALYSIS: | | | |
|---|---|---|---|
| Calculated for $C_{27}H_{32}F_5N_3O_2 \cdot$ $2(C_4H_4O_4)$ | 55.48% C | 5.28% H | 5.55% N |
| Found: | 55.32% C | 5.38% H | 5.48% N |

EXAMPLE 26
(EXO)-8-[(DIMETHYLPHOSPHINYL)METHYL]-3-(2,3,4,5,6-PENTAFLUOROPHENOXY)-8-AZABICYCLO[3.2.1]OCTANE

To a mixture of 5 g of potassium carbonate and 4.0 g of (exo)-3-(2,3,4,5,6-pentafluorophenoxy)-8-azabicyclo[3.2.1]octane in 100 ml of dimethylformamide was added 3.54 g of dimethylphosphinylmethyl chloride. The reaction mixture was then stirred at 85° C. for thirty hours, cooled, and filtered. The filtrate was poured into water and extracted with ethyl acetate. The organic layer was washed with water followed by a saturated sodium chloride solution, dried over anhydrous magnesium sulfate, filtered, and concentrated. The concentrate was purified by means of high pressure liquid chromatography (silica gel; elution with ethyl acetate followed by 5% methanol/dichloromethane) to yield 2.9 g (54.10%) of (exo)-8-[(dimethylphosphinyl)methyl]-3-(2,3,4,5,6-pentafluorophenoxy)-8-azabicyclo[3.2.1]octane, m.p. 66°–68° C.

| ANALYSIS: | | | |
|---|---|---|---|
| Calculated for $C_{16}H_{19}F_5NO_2P$: | 50.13% C | 4.96% H | 3.66% N |
| Found: | 49.94% C | 5.11% H | 3.37% N |

EXAMPLE 27
(EXO)-3-(2,3,4,5,6-PENTAFLUOROPHENOXY)-8-[3-(2-METHYLINDOL-3-YL)PROPYL]-8-AZABICYCLO[3.2.1]OCTANE HYDROCHLORIDE

A mixture of 3.5 g of (exo)-3-(2,3,4,5,6-pentafluorophenoxy)-8-azabicyclo[3.2.1]octane, 3.9 g of 3-(2-methylindol-3-yl)propyl phenyl sulfonate, 10 g of potassium carbonate and 80 ml of dry dimethylformamide was stirred at 90° C. for four hours. The reaction mixture was then cooled, poured into 200 ml of water, stirred for five minutes, and extracted with ethyl acetate. The organic layer was washed with water followed by a saturated sodium chloride solution, dried over anhydrous magnesium sulfate, filtered, and concentrated. The concentrate was purified by means of high pressure liquid chromatography (silica gel; elution with ethyl acetate) to yield 4.2 g of (exo)-3-(2,3,4,5,6-pentafluorophenoxy)-8-[3-(2-methylindol-3-yl)propyl]-8-azabicyclo[3.2.1]octane as an oil. The oil was dissolved in diethyl ether and treated with etheral hydrogen chloride to precipitate 3.4 g (57%) of the corresponding hydrochloride salt, m.p. 250° C.

| ANALYSIS: | | | |
|---|---|---|---|
| Calculated for $C_{25}H_{25}F_5N_2O \cdot HCl$: | 59.94% C | 5.23% H | 5.59% N |
| Found: | 59.78% C | 5.22% H | 5.78% N |

EXAMPLE 28
(EXO)-3-(2,3,4,5,6-PENTAFLUOROPHENOXY)-8-[(N-METHYLAMINO)CARBONYL]-8-AZABICYCLO[3.2.1]OCTANE

A solution of 4.0 g of (exo)-3-(2,3,4,5,6-pentafluorophenoxy)-8-azabicyclo[3.2.1]octane in 50 ml of benzene was treated, dropwise, with a solution of 0.80 g of methylisocyanate in 10 ml of benzene and stirred for four hours at ambient temperature. Evaporation of the solvent afforded a solid which was purified by means of high pressure liquid chromatography (silica gel; elution with 50% ethyl acetate/dichloromethane) to yield 3.4 g (69.4%) of (exo)-3-(2,3,4,5,6-pentafluorophenoxy)-8-[(N-methylamino)carbonyl]-8-azabicyclo[3.2.1]octane, m.p. 180°–182° C.

| ANALYSIS: | | | |
|---|---|---|---|
| Calculated for $C_{15}H_{15}F_5N_2O_2$: | 51.43% C | 4.29% H | 8.00% N |
| Found: | 51.41% C | 4.39% H | 8.07% N |

What is claimed is:

1. A convulsion treating composition comprising an inert convulsion-treating adjunct and, as the active ingredient, an effective anticonvulsant amount of a compound of the formula

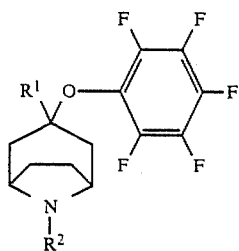

wherein $R^1$ is hydrogen or aryl and $R^2$ is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

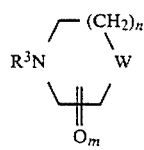

wherein n is an integer having a value of zero or 1, m is an integer having a value of zero or 1, W is $CH_2$, or $NR^{3a}$ wherein $R^{3a}$ is hydrogen, loweralkyl or aryl, and $R^3$ is loweralkylene, or loweralkynylene, and a group of the formula

where $R^4$ is $CH(Cl)CH_3$, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy.

2. A method of treatment which comprises administering to a mammal in need of relief from convulsions a pharmaceutically effective amount of a compound of the formula

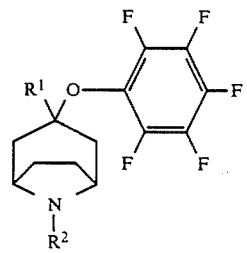

wherein $R^1$ is hydrogen or aryl and $R^2$ is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

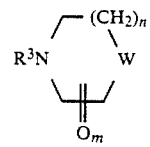

wherein n is an integer having a value of zero or 1, m is an integer having a value of zero or 1, W is $CH_2$, or $NR^{3a}$ wherein $R^{3a}$ is hydrogen, loweralkyl or aryl, and $R^3$ is loweralkylene, or loweralkynylene, and a group of the formula

where $R^4$ is $CH(Cl)CH_3$, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy.

3. A depression treating composition comprising an inert depression-treating adjunct and, as the active ingredient, an effective anti-depressant amount of a compound of the formula

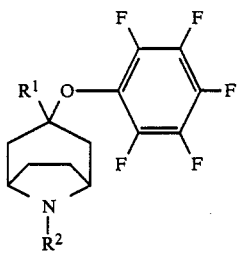

wherein $R^1$ is hydrogen or aryl and $R^2$ is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

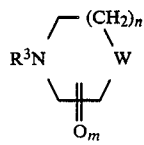

wherein n is an integer having a value of zero or 1, m is an integer having a value of zero or 1, W is $CH_2$, or $NR^{3a}$ wherein $R^{3a}$ is hydrogen, loweralkyl or aryl, and $R^3$ is loweralkylene, or loweralkynylene, and a group of the formula

where $R^4$ is $CH(Cl)CH_3$, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy.

4. A method of treatment which comprises administering to a mammal in need of relief from depression a pharmaceutically effective amount of a compound of the formula

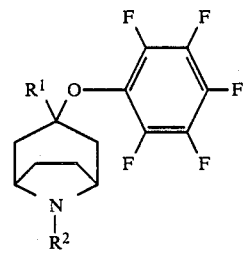

wherein $R^1$ is hydrogen or aryl and $R^2$ is a monovalent radical elected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkyoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

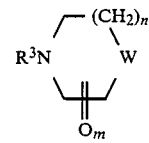

wherein n is an integer having a value of zero or 1, m is an integer having a value of zero or 1, W is $CH_2$, or $NR^{3a}$ wherein $R^{3a}$ is hydrogen, loweralkyl or aryl, and $R^3$ is loweralkylene, or loweralkynylene, and a group of the formula

where $R^4$ is $CH(Cl)CH_3$, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy and a pharmaceutically acceptable carrier therefor.

5. An antihypertensive composition comprising an effective blood pressure lowering amount of a compound of the formula

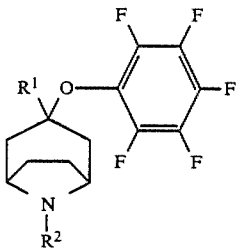

wherein R¹ is hydrogen or aryl and R² is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

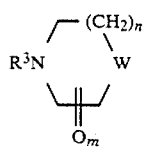

wherein n is an integer having a value of zero or 1, m is an integer having a value of zero or 1, W is CH₂, or NR³ₐ wherein R³ₐ is hydrogen, loweralkyl or aryl, and R³ is loweralkylene, or loweralkynylene, and a group of the formula

where R⁴ is CH(Cl)CH₃, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy and a pharmaceutically acceptable carrier therefor.

6. A method of treating a patient in need of relief from high blood pressure which comprises administering to the patient an effective amount of a compound of the formula

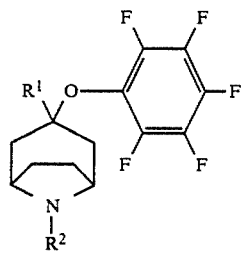

wherein R¹ is hydrogen or aryl and R² is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

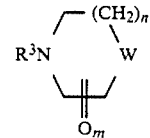

wherein n is an integer having a value of zero or 1, m is an integer having a value of zero or 1, W is CH₂, or NR³ₐ wherein R³ₐ is hydrogen, loweralkyl or aryl, and R³ is loweralkylene, or loweralkynylene, and a group of the formula

where R⁴ is CH(Cl)CH₃, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy.

7. A pain alleviating composition comprising an inert pain-alleviating adjunct and, as the active ingredient, as amount effective in alleviating pain of a compound of the formula

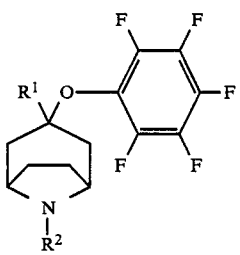

wherein R¹ is hydrogen or aryl and R² is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

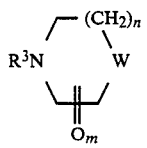

wherein n is an integer having a value of zero or 1, m is an integer having a value of zero or 1, W is CH₂, or NR³ᵃ wherein R³ᵃ is hydrogen, loweralkyl or aryl, and R³ is loweralkylene, or loweralkynylene, and a group of the formula

where R⁴ is CH(Cl)CH₃, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy.

8. A method of alleviating pain comprising administering to a mammal in need of pain alleviation a pain alleviating effective amount of a compound of the formula

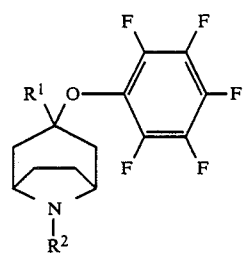

wherein R¹ is hydrogen or aryl and R² is a monovalent radical selected from the group consisting of hydrogen, cyano, loweralkyl, cycloalkylloweralkyl, arylloweralkyl, heteroarylloweralkyl, formyl, loweralkylcarbonyl, loweralkoxycarbonyl, (arylloweralkyl)carbonyl, thioformyl, loweralkylthiocarbonyl, loweralkoxythiocarbonyl, (arylloweralkyl)thiocarbonyl, aminocarbonyl, (loweralkylamino)carbonyl, (diloweralkylamino)carbonyl, (arylamino)carbonyl, aminocarbonyl, (loweralkylamino)thiocarbonyl, (diloweralkylamino)thiocarbonyl, (arylamino)thiocarbonyl, aminoloweralkyl, (loweralkylamino)loweralkyl, (diloweraminoalkyl)loweralkyl, (diloweralkylphosphinyl)loweralkyl, a group of the formula

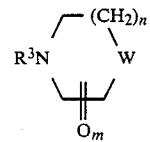

wherein n is an integer having a value of zero or 1, m is an integer having a value of zero or 1, W is CH₂, or NR³ᵃ wherein R³ᵃ is hydrogen, loweralkyl or aryl, and R³ is loweralkylene, or loweralkynylene, and a group of the formula $$\overset{O}{\underset{}{\|}}_{COR^4}$$

where R⁴ is CH(Cl)CH₃, the term aryl in each occurrence signifying a phenyl group optionally substituted by one or more substituents selected from the group consisting of halogen, loweralkyl, loweralkoxy and trifluoromethyl; the term cycloalkyl in each occurrence signifying saturated carbocyclic group having from 3 to 7 carbon atoms; and the term heteroaryl in each occurrence signifying an aromatic heterocyclic mono- or dicyclic radical selected from the group consisting of benzisoxazolyl, indolyl, benzimidazoyl, and pyrrolidinyl optionally substituted by one or more substituents selected from the group consisting of halogen, loweralkyl and loweralkoxy.

* * * * *